United States Patent [19]

Furutaka et al.

[11] Patent Number: 4,929,318
[45] Date of Patent: May 29, 1990

[54] PROCESS FOR PREPARING HALOGENATED ALKANE

[75] Inventors: Yasuhisa Furutaka; Hirokazu Aoyama; Tsunetoshi Honda, all of Osaka, Japan

[73] Assignee: Daikin Industries Ltd., Osaka, Japan

[21] Appl. No.: 247,354

[22] Filed: Sep. 21, 1988

[30] Foreign Application Priority Data

Sep. 22, 1987 [JP] Japan .............................. 62-238149
Dec. 29, 1987 [JP] Japan .............................. 62-332719

[51] Int. Cl.$^5$ ............................................ B01J 19/12
[52] U.S. Cl. .......................... 204/157.6; 204/157.94; 204/158.11
[58] Field of Search .............. 204/157.6, 59 F, 158.11, 204/157.94

[56] References Cited

U.S. PATENT DOCUMENTS 4,060,469  4/1977  Sweeney ........................ 204/158.11
4,422,913  12/1983  Larsen ............................ 204/158.11

FOREIGN PATENT DOCUMENTS 451378  9/1948  Canada ........................... 204/157.94

Primary Examiner—John F. Niebling
Assistant Examiner—Isabelle Rodriguez

[57] ABSTRACT

A halogenated alkane of the formula $$R-CHXY \qquad (I)$$

wherein R is a trifluoromethyl group, a chlorodifluoromethyl group, a dichlorofluoromethyl group, a chlorofluoromethyl group, a difluoromethyl group, a fluoromethyl group or a 2-chloro-1,1,2,2-tetrafluoroethyl group, and X and Y are the same or different and a hydrogen atom, a chlorine atom or a fluorine atom can be prepared at a high yield by reducing a halogenated alkane of the formula:

$$R-CClXY \qquad (II)$$

wherein R, X and Y are the same as defined above with the irradiation of light having a wavelength of not longer than 300 nm in an oxygen-free reaction atmosphere in the presence of 3 to 10 moles of an alcohol per mole of the halogenated alkane of the formula (II) or in the presence of 0.1 to 10 moles of an alcohol per mole of the halogenated alkane of the formula (II) and an alkali.

3 Claims, No Drawings

PROCESS FOR PREPARING HALOGENATED ALKANE

BACKGROUND OF THE INVENTION

1. Field of the Invention

The present invention relates to a process for preparing a halogenated alkane. More particularly, the present invention relates to a process for preparing a halogenated alkane by reducing a halogenated alkane in an alcohol with light irradiation.

The halogenated alkanes are useful as foaming agents, propellants for aerosols, refrigerants, solvents and the like.

2. Description of the Related Art

Known processes for reducing halogenated hydrocarbons include a process for catalytically reducing the halogenated hydrocarbons in the presence of a palladium catalyst (cf. Japanese Pat. Publication No. 38131/1981), a process for reducing a raw material with zinc and an alcohol (cf. Japanese Pat. Kokai Publication No. 222038/1983), a process for reducing a raw material with potassium acetate and an alcohol (cf. Czechoslovakian Pat. No. 144,073) and a process for reducing a raw material with a sodium amalgam (cf. European patent application No. 164954).

These processes have various drawbacks such as difficult control of the reactions, high costs and the like. Therefore, they are not technically preferable processes.

The reduction of the halogenated hydrocarbon with light is disclosed in Czechoslovakian Pat. No. 136,735, but this process has some drawbacks such as poor reproducibility, a low reaction rate, intermediate termination of the reaction which results in poor conversion.

SUMMARY OF THE PRESENT INVENTION

An object of the present invention is to provide a process for preparing a halogenated alkane by photoreduction of a raw material halogenated hydrocarbon, which does not suffer from the drawbacks of the above described conventional processes.

Accordingly, the present invention provides a process for preparing a halogenated alkane of the formula:

R—CHXY          (I)

wherein R is a trifluoromethyl group, a chlorodifluoromethyl group, a dichlorofluoromethyl group, a chlorofluoromethyl group, a difluoromethyl group, a fluoromethyl group or a 2-chloro-1,1,2,2-tetrafluoroethyl group, and X and Y are the same or different and a hydrogen atom, a chlorine atom or a fluorine atom, which comprises reducing a halogenated alkane of the formula:

R—CCIXY          (II)

wherein R, X and Y are the same as defined above with the irradiation of light having a wavelength of not longer than 300 nm in an oxygen-free reaction atmosphere in the presence of 3 to 10 moles of an alcohol per mole of the halogenated alkane of the formula (II) or in the presence of 0.1 to 10 moles of an alcohol per mole of the halogenated alkane of the formula (II) and an alkali.

The present invention has been completed based on the findings that the reaction proceeds with difficulty if oxygen is present in the reaction system, to proceed the reaction effectively, light having a specific wavelength should be irradiated, to prevent the intermediate termination of the reaction, a specific amount of the alcohol should be used based on the amount of the raw material halogenated hydrocarbon, and the presence of the alkali further accelerates the reaction.

DETAILED DESCRIPTION OF THE INVENTION

Most of the halogenated alkanes (II) are commercially available, and those which are not commercially available can be prepared by known processes. For example, $CF_3$—$CCl_3$ can be prepared by rearrangement of $CCl_2F$—$CClF_2$ (F—113), and $CF_3$—$CCl_2F$ can be prepared by fluorination of $CF_3$—$CCl_3$.

The first feature of the present invention is purging of oxygen from the reaction atmosphere with an inert gas (e.g. nitrogen, helium, argon, etc.) before the start of the reaction. If the reaction were started without purging oxygen, the reaction rate would be very low or the reaction would be terminated at low conversion The second feature of the present invention is irradiation of the reaction system with light having a wavelength of not longer than 300 nm. Therefore, as an illuminant, a lamp which emits a large amount of light having a shorter wavelength is preferably used. An example of the preferred lamp is low pressure mercury lamp 90% of light beams emitted from which have the wavelength of 254 nm. A jacket of the lamp and at least a part of the reactor through which light is irradiated are preferably made of quartz. When the reduction is carried out in the presence of the alkali, a below described reaction-inhibiting condensation product is not formed so that the desired product is obtained in a good yield even when Pyrex glass is used in place of the quartz glass. In this case, as a strength of light having a wavelength of 300 nm or less is weakened, the reaction rate is decreased. As a commercially usable lamp, a high pressure mercury lamp which emits light having a wavelength of 300 nm or less can be used.

The third feature of the present invention is that 3 to 10 moles, preferably 5 to 10 moles of alcohol is used per mole of the halogenated alkane (II). A cause for the intermediate termination of the conventional photoreduction was studied. As a result, it has been found that a condensation product is formed by the reaction of a carbonyl compound and hydrogen chloride which are formed during the photoreduction and suppresses the photoreduction. For example, when isopropanol is used as the alcohol, mesityl oxide which is a condensation product of acetone is formed. Since mesityl oxide will absorbs light having a wavelength not longer than 300 nm, for example, it absorbs light $10^6$ times more than $CF_2Cl$—$CFCl_2$ as the raw material, the reaction is suppressed or terminated. Further, the formation of the condensation product is influenced by the amount of the alcohol. When the amount of the alcohol is increased, the formation of the condensation product can be reduced to such an amount that has little influence on the reaction. As described below, when the alkali is present in the reaction system, the amount of the alcohol can be reduced to 0.1 to 10 moles per mole of the halogenated alkane (II).

As the alcohol to be used in the process of the present invention, isopropanol is preferred in view of reactivity and low cost, although other alcohols such as methanol, ethanol, sec.-butanol, cyclohexanol and the like can be used.

The reaction in the absence of the alkali can be carried out at a temperature of $-40°$ to $+100°$ C., preferably a low temperature of $-40°$ to $0°$ C. By keeping the reaction temperature comparatively low, the same effects as achieved by increasing the amount of the alcohol can be achieved. Therefore, by lowering the reaction temperature, the amount of the alcohol can be reduced.

The presence of the alkali in the reaction system is found to be effective to suppress the formation of the condensation product. That is, when the alkali is present in the reaction system, the reaction is not terminated and the conversion of the raw material can be increased in a shorter time. In addition, when the alkali is present, the amount of the alcohol can be reduced to 0.1 to 10 moles per mole of the halogenated alkane (II), which is smaller than the amount required when the alkali is not present. Further, the reaction temperature is not limited to a comparatively low temperature and is usually from $-10°$ to $100°$ C.

As the alkali, any one may be used. Preferred examples of the alkali are potassium bicarbonate, sodium bicarbonate, potassium carbonate, sodium carbonate, calcium hydroxide, ammonia and mixtures thereof.

The amount of the alkali is at least an equimolar amount of a monoacid base or at least a half equimolar amount of a diacid base per mole of the halogenated alkane (II).

The reaction temperature varies with boiling points of the raw material and/or the product. Usually, it is from $-10°$ C. to $+100°$ C.

The reaction can be carried out batchwise or continuously. Commercially, the continuous reaction is preferred.

PREFERRED EMBODIMENTS OF THE INVENTION

The present invention will be illustrated by following Examples.

EXAMPLE 1

In a quartz made 100 ml flask equipped with a reflux condenser, isopropanol (45 g, 0.75 mole) and $CF_2Cl$—$CFCl_2$ (14 g, 0.075 mole) were charged. In the flask, nitrogen was introduced at a flow rate of 30 ml/min. at 20° C. for 30 minutes. Then, the reaction mixture was irradiated by a 15 W low pressure mercury lamp for 3 hours while stirring. Gas chromatographic analysis of the reaction mixture revealed that the conversion of the raw material was 60% after 1 (one) hour and 85% after 3 hours. After 3 hours, the reaction was stopped, and the reaction mixture was rectified to obtain $CF_2Cl$—$CFClH$ at 28° C. (8.9 g, 0.056 mole). Yield, 75%.

EXAMPLE 2

In a quartz made 100 ml flask equipped with a reflux condenser, isopropanol (45 g, 0.75 mole) and $CF_2Cl$—$CFCl_2$ (14 g, 0.075 mole) were charged. In the flask, nitrogen was introduced at a flow rate of 30 ml/min. at 20° C. for 30 minutes. Then, the reaction mixture was irradiated by a 400 W high pressure mercury lamp for 2 hours while stirring. In a short time, the interior temperature slightly rose and a product $CF_2Cl$—$CFClH$ was refluxed. Gas chromatographic analysis of the reaction mixture revealed that the conversion of the raw material was 80% after 1 hour and 91% after 2 hours. After 2 hours, the reaction was stopped, and the reaction mixture was rectified to obtain $CF_2Cl$—$CFClH$ at 27° C. (9.2 g, 0.06 mole). Yield, 80%.

EXAMPLE 3

In a quartz made 100 ml flask equipped with a reflux condenser, isopropanol (36 g, 0.6 mole), $CF_2Cl$—$CFCl_2$ (37.5 g, 0.2 mole) and sodium bicarbonate (17 g, 0.2 mole) were charged. In the flask, nitrogen was introduced at a flow rate of 30 ml/min. at 20° C. for 30 minutes. Then, the reaction mixture was irradiated by a 75 W high pressure mercury lamp for 2 hours while stirring. In a short time, the interior temperature slightly rose and a product, $CF_2Cl$—$CFClH$ was refluxed. Gas chromatographic analysis of the reaction mixture revealed that the conversion of the raw material was 100% after 2 hours. Then, the reaction was stopped, and the reaction mixture was rectified to obtain $CF_2Cl$—$CFClH$ at 27° C. (26.0 g, 0.17 mole). Yield, 85%.

EXAMPLE 4

In the same manner as in Example 2 but using $CF_3$—$CCl_3$ in place of $CF_2Cl$—$CFCl_2$ and a 75 W high pressure mercury lamp in place of the 400 W high pressure mercury lamp, the reaction was carried out. Gas chromatographic analysis of the reaction mixture revealed that the conversion of the raw material was 65% after 1 hour and 80% after 3 hours.

EXAMPLE 5

In a quartz made 100 ml flask equipped with a reflux condenser, isopropanol (36 g, 0.6 mole), $CF_3$—$CCl_3$ (37.5 g, 0.2 mole) and potassium carbonate (14 g, 0.1 mole) were charged. In the flask, nitrogen was introduced at a flow rate of 30 ml/min. at 20° C. for 30 minutes. Then, the reaction mixture was irradiated by a 400 W high pressure mercury lamp for 3 hours while stirring. In a short time, the interior temperature slightly rose and a product, $CF_3$—$CHCl_2$ was refluxed. Gas chromatographic analysis of the reaction mixture revealed that the conversion of the raw material was 98% after 3 hours. Then, the reaction was stopped, and the reaction mixture was rectified to obtain $CF_3$—$CHCl_2$ at 27° C. (27.5 g, 0.18 mole, Yield, 90%) and a small amount of $CF_3$—$CH_2Cl$.

EXAMPLE 6

In an internal irradiation type flask having a quartz made light receiving part and a content volume of about 2 liters, isopropanol (960 g, 16 moles) and potassium carbonate (375 g, 2.7 moles) were charged. In the flask, nitrogen was introduced at 50 ml/min. at 20° C. for 40 minutes. Then, $CF_2Cl$—$CFCl_2$ (1,000 g, 5.33 moles) was dropwise added over about 3 hours while irradiating the reaction mixture by a 400 W high pressure mercury lamp. After the addition of the raw material, stirring and irradiation were continued for 2 hours. Gas chromatographic analysis of the reaction mixture revealed that the conversion of the raw material was 99%. The reaction mixture was thoroughly cooled, filtrated under pressure and then rectified to obtain $CF_2Cl$—$CFClH$ (765 g, 0.5 mole). Yield, 94%.

EXAMPLE 7

In a quartz made 100 ml flask equipped with a reflux condenser, isopropanol (45 g, 0.75 mole) and $CF_2Cl$—$CFCl_2$ (47 g, 0.25 mole) were charged. In the flask, nitrogen was introduced at a flow rate of 30 ml/min. at 20° C. for 30 minutes. Then, the reaction mixture was irradiated by a 75 W high pressure mercury lamp for 3 hours while introducing ammonia gas at a flow rate of 30 ml/min. Gas chromatographic analysis of the reaction mixture revealed that the conversion of the raw material was 98%.

EXAMPLE 8

In the same manner as in Example 3 but using potassium hydroxide (7.4 g) in place of sodium bicarbonate, the reaction was carried out. Gas chromatographic analysis of the reaction mixture revealed that the conversion of the raw material was 100% after 3 hours.

EXAMPLE 9

In an internal irradiation type flask having a quartz made light receiving part and a content volume of about 2 liters, isopropanol (720 g, 12 moles) and sodium carbonate (212 g, 2 moles) were charged. In the flask, nitrogen was introduced at a flow rate of 50 ml/min. at 20° C. for 40 minutes. Then, $CF_2Cl$—$CFCl_2$ containing about 10% of $CF_2Cl$—$CCl_3$ (816 g, 4 moles) was dropwise added over about 1 hour while irradiating the reaction mixture by a 400 W high pressure mercury lamp. After the addition of the raw material, stirring and irradiation were continued for 2 hours. Gas chromatographic analysis of the reaction mixture revealed that the conversion of the raw material was about 98% and the selectivity of $CFCl_2$—$CFClH$ ($CF_2Cl$—$CCl_2H$) was about 90% and confirmed the formation of further reduced products, $CFClH$—$CFClH$ and $CF_2Cl$—$CH_2Cl$.

Further, sodium carbonate (212 g, 2 moles) was added to the flask and irradiation was continued for 3 hours. The reaction mixture was thoroughly cooled, filtrated under pressure and then rectified to collect fractions having boiling points in a range from 57° C. to 60° C. The collected product was washed with iced water to obtain $CFClH$—$CFClH$ (445 g). Yield, 92%.

EXAMPLE 10

In Pyrex glass made 2 liter flask, isopropanol (960 g, 16 moles), sodium bicarbonate (462 g, 5.5 moles) and $CF_2Cl$—$CFCl_2$ (1,000 g, 5.33 moles) were charged. In the flask, nitrogen was introduced at a flow rate of 50 ml/min. at 20° C. for 1 hour. Then, the flask was irradiated by a 400 W high pressure mercury lamp. After 4 hours, the conversion of the raw material was 99%. The reaction mixture was thoroughly cooled, filtrated under pressure and then rectified to obtain $CF_2Cl$—$CFClH$ (772 g, 5.05 moles). Yield, 94.7%.

EXAMPLE 11

In a quartz made 100 ml flask equipped with a reflux condenser, isopropanol (9 g, 0.15 mole), $CF_2Cl$—$CFCl_2$ (56.3 g, 0.3 mole) and sodium bicarbonate (12.6 g, 0.15 mole) were charged. In the flask, nitrogen was introduced at a flow rate of 30 ml/min. at 20° C. for 30 minutes. Then, the reaction mixture was irradiated by a 400 W high pressure mercury lamp while stirring. After 4 hours, the conversion of the raw material and isopropanol were 48% and 98%, respectively.

EXAMPLE 12

In the same manner as in Example 3 but using cyclohexanol (45 g, 0.4 mole) in place of isopropanol, the reaction was carried out. Gas chromatographic analysis of the reaction mixture revealed that the conversion of the raw material was 98%.

EXAMPLE 13

In an internal irradiation type flask having a quartz made light receiving part and a content volume of about 2 liters, isopropanol (960 g, 16 moles) and $CF_2Cl$—$CFCl_2$ (1,000 g, 5.33 moles) were charged. In the flask, nitrogen was introduced at a flow rate of 50 ml/min. at −20° C. for 40 minutes. Then, the flask was irradiated by a 400 W high pressure mercury lamp for 4 hours while keeping that temperature by external cooling. Gas chromatographic analysis of the reaction mixture revealed that the conversion of the raw material was about 95%.

EXAMPLE 14

In an internal irradiation type flask having a quartz made light receiving part and a content volume of about 2 liters, isopropanol (720 g, 12 moles) and sodium carbonate (212 g, 2 moles) were charged. In the flask, nitrogen was introduced at a flow rate of 50 ml/min. at 20° C. for 40 minutes. Then, $CF_2ClCF_2CCl_3$ (1,016 g, 4 moles) was dropwise added over about 1 hour while irradiating the reaction mixture by a 400 W high pressure mercury lamp. After the addition of the raw material, stirring and irradiation were continued for 4 hours. Gas chromatographic analysis of the reaction mixture revealed that the conversion of the raw material was about 96% and the selectivity of $CF_2ClCF_2CHCl$ was 94% and confirmed the formation of further reduced product, $CF_2ClCF_2CH_2Cl$.

Further, sodium carbonate (212 g, 2 moles) was added to the flask and irradiation was continued for 5 hours. The reaction mixture was thoroughly cooled, filtrated under pressure and then rectified to collect fractions having boiling points in a range from 66° C. to 70° C. The collected product was washed with iced water to obtain $CF_2ClCF_2CH_2Cl$ (666 g). Yield, 90%.

What is claimed is:

1. A process for preparing a halogenated alkane of the formula:

$$R\text{—}CHXY \qquad (I)$$

wherein R is a trifluoromethyl group, a chlorodifluoromethyl group, a dichlorofluoromethyl group, a chlorofluoromethyl group, a difluoromethyl group, a fluoromethyl group or a 2-chloro-1,1,2,2-tetrafluoroethyl group, and X and Y are the same or different and are selected from hydrogen, chlorine or fluorine, which comprises reducing a halogenated alkane of the formula:

$$R\text{—}CClXY \qquad (II)$$

wherein R, X and Y are the same as defined above with the irradiation of light having a wavelength of not longer than 300 nm in an oxygen-free reaction atmosphere in the presence of 3 to 10 moles of an alcohol per mole of the halogenated alkane of the formula (II) or in the presence of 0.1 to 10 moles of an alcohol per mole of the halogenated alkane of the formula (II) and an alkali.

2. The process according to claim 1, wherein the alcohol is isopropanol.

3. The process according to claim 1, wherein the alkali is selected from the group consisting of potassium bicarbonate, sodium bicarbonate, potassium carbonate, sodium carbonate, calcium hydroxide and ammonia.

* * * * *